United States Patent [19]
Schroit et al.

[11] Patent Number: 4,983,397
[45] Date of Patent: Jan. 8, 1991

[54] PHARMACEUTICAL COMPOSITIONS CONSISTING OF ACYLATED PHOSPHOLIPIDS

[75] Inventors: Alan J. Schroit; Rajiv Nayar, both of Houston, Tex.

[73] Assignee: Board of Regents, University of Texas System, Houston, Tex.

[21] Appl. No.: 888,601

[22] Filed: Jul. 21, 1986

Related U.S. Application Data

[63] Continuation-in-part of Ser. No. 766,625, Aug. 19, 1985, abandoned.

[51] Int. Cl.$^5$ ............................ A61K 9/52; B01J 13/02
[52] U.S. Cl. .................................. 424/450; 428/402.2; 436/829; 514/34; 514/974
[58] Field of Search ...................... 424/417, 85.5, 450; 264/4.1, 4.3, 4.6; 428/402.2; 436/829; 514/974, 34

[56] References Cited

U.S. PATENT DOCUMENTS 4,515,736 5/1985 Deamer .................................. 424/9
4,622,219 11/1986 Haynes .................................. 424/38

FOREIGN PATENT DOCUMENTS 1523965 9/1978 United Kingdom .
8303383 10/1983 World Int. Prop. O. .

OTHER PUBLICATIONS

M. B. Yatvin et al., *Science*, 210, pp. 1253-1255 (1980).
Harma Ellens et al., *Biochemistry* 1984, 23, 1532-1538.

*Primary Examiner*—Ronald W. Griffin
*Attorney, Agent, or Firm*—Mathews, Woodbridge & Collins

[57] ABSTRACT

Liposome dispersions are prepared from (a) a synthetic phospholipid of the cephaline type in which the amino group is monoacylated with a dicarboxylic acid; (b) a synthetic phospholipid of the cephaline type; and (c) one or more compounds having pharmacological activity. The mixture optionally can contain phospholipids of natural sources and a pharmaceutical carrier solution buffered to pH 7.0 to 7.8.

11 Claims, No Drawings

PHARMACEUTICAL COMPOSITIONS CONSISTING OF ACYLATED PHOSPHOLIPIDS

CROSS-REFERENCE TO RELATED APPLICATIONS

This is a continuation-in-part of Ser. No. 766,625 filed Aug. 19, 1985, now abandoned.

Subject matter of the present invention are pharmaceutical compositions containing acylated phosphatidylethanolamine derivatives, phosphatidylethanolamine and compounds having pharmacological properties. The present invention also relates to mixtures of the acylated phosphatidylethanolamine derivatives and phosphatidylethanolamine, a process for the preparation of the pharmaceutical compositions, and a method of use for the pharmaceutical compositions.

The pharmaceutical compositions according to the present invention are being administered in the form of liposomes.

Pharmaceutical administration systems based on liposomes have been described in the general review issued by G. Gregoriadis, Liposome Technology, Vol. II, Incorporation of Drugs, Proteins and Genetic Material, CRC Press 1984. Such systems have the advantage that biologically active material can be introduced into tissues by phagocytosis, especially into tissues of the reticulo-endothelial system. For example, a transport mechanism is known how antibiotics are being introduced into infected tissues by phagocytosis thus causing the improved removal or destruction of the infecting microorganism. Endocytosis also is a helpful mechanism in the combat of centres of inflammation. Antirheumatic pharmaceuticals encapsulated in liposomes are preferably introduced into infected tissues as compared to "healthy" tissues. Moreover, cytostatic agents, commonly known as "anticancer drugs", when encapsulated in liposomes, can be introduced into specific organs of the reticuloendothelial system (liver, spleen or marrow). Additionally, due to filtration in the capillaries of the lung and subsequent transport by migrating monocytes, biologically active material, for example compounds having immunomodulatory properties, can be concentrated in alveolar macrophages. This results in an improved action on metastatic lung tumours and in a simultaneous reduction of toxicity.

It has now surprisingly been found that the uptake of liposomes and their endocytosis by macrophages, especially alveolar macrophages, is increased whenever acylated phosphatidylethanolamine derivatives are incorporated in the shell structure of the liposomes.

The present invention relates to pharmaceutical compositions consisting of (a) a phospholipid of the formula

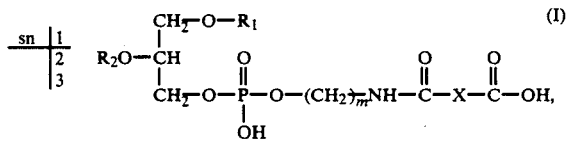

wherein m represents two or three, $R_1$ and $R_2$ independently of each other represent alkyl, alkenyl, or acyl each having from 10 to 20 carbon atoms, X represents the direct bond, $C_1$–$C_4$-alkylene, $C_2$–$C_4$-alkenylene, or $C_1$–$C_4$-alkylene or $C_2$–$C_4$-alkenylene substituted by hydroxy or a pharmaceutically acceptable salt thereof, (b) a phospholipid of the formula

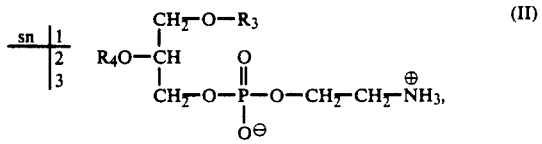

wherein $R_3$ and $R_4$ represent the acyl group of a saturated or an unsaturated carboxylic acid having from 10 to 20 carbon atoms and 1-2 double bonds, (c) a compound or a mixture of compounds having pharmacological activity, and, optionally, (d) a lipid selected from the group consisting of phosphatidylcholine, phosphatidylserine, phosphatidylinositol, phosphatidylglycerol, cardiolipin and cholesterol and its derivatives, and, optionally, a pharmaceutically acceptable carrier solution buffered to pH 7.0–7.8, and, optionally, pharmaceutically acceptable additives.

In the context of the description of the present invention, the general terms employed hereinbefore and hereinafter preferably have the following meanings:

The terms "lower" used in connection with definitions of organic radicals, for example lower alkyl, lower alkylene, lower alkoxy, lower alkanoyl, etc., means that such organic radicals, unless expressly defined otherwise, contain up to 7, preferably up to 4, carbon atoms.

The nomenclature of the phospholipids of the formulae I and II is in agreement with the recommendations of the IUPAC and IUB Commission on Biochemical Nomenclature (CBN) according to the Eur. J. of Biochem. 79, 11–21 (1977) "Nomenclature of Lipids" (sn-nomenclature, stereospecific numbering).

Unless indicated otherwise, generic names proposed by the World Health Organisation (WHO) (Recommended International Nonproprietary Names) are used to define the active ingredients, which names have been taken from the standard text book "Pharmazeutische Chemie" (E. Schröder, C. Rufer and R. Schmiechen, Thieme Verlag Stuttgart, 1982) and the Merck Index (Tenth Edition).

In the synthetic phospholipid of the formula I (component a) m is preferably two.

Alkyl $R_1$ and/or $R_2$ is preferably straight-chained with an even number from 10 to 20 carbon atoms, for example n-decyl, n-dodecyl, n-tetradecyl, n-hexadecyl, n-octadecyl or n-icosyl.

Alkenyl $R_1$ and/or $R_2$ is preferably straight-chained with an even number from 12 to 20 carbon atoms and a double bond, for example 9-cis-dodecenyl, 9-cis-tetradecenyl, 9-cis-hexadecenyl, 6-cis-octadecenyl, 6-trans-octadecenyl, 9-cis-octadecenyl, 9-trans-octadecenyl or 9-cis-icosenyl.

Acyl $R_1$ and/or $R_2$ is preferably straight-chained with an even number from 10–20 carbon atoms, for example $C_{10}$–$C_{20}$-alkanoyl or $C_{10}$–$C_{20}$-alkenoyl.

Alkanoyl $R_1$ and/or $R_2$ is preferably n-decanoyl, n-dodecanoyl, n-tetradecanoyl, n-hexadecanoyl, n-octadecanoyl and n-icosanoyl.

Alkenoyl $R_1$ and/or $R_2$ is preferably 9-cis-dodecenoyl, 9-cis-tetradecenoyl, 9-cis-hexadecenoyl, 6-cis-octadecenoyl, 6-trans-octadecenoyl, 9-cis-octadecenoyl, 9-trans-octadecenoyl, 11-cis-octadecenoyl and 9-cis-icosenoyl.

X defined as $C_1$–$C_4$-alkylene is straight chained or branched $C_1$–$C_4$-alkylene, for example methylene, 1,1- ethylene, 1,1-, 1,2- or 1,3-propylene or, preferably, 1,2-ethylene.

X defined as $C_2$–$C_4$-alkenylene is preferably straight chained alkenylene, for example vinylene, propylene, or 1,2- or 2,3-butylene.

X defined as $C_1$–$C_4$-alkylene or $C_2$–$C_4$-alkenylene substituted by hydroxy is preferably straight chained $C_1$–$C_4$-alkylene substituted by 1 or, depending on the number of carbon atoms, up to 4 hydroxy groups, for example 1-hydroxy-1,2-ethylene, 1,2-dihydroxy-1,2-ethylene, 1- or 2-hydroxy-1,3-propylene or 1,2-dihydroxy-1,3-propylene.

A pharmaceutically acceptable salt of the phospholipid (I) is preferably formed by reaction with one or two equivalents of dilute aqueous alkalimetal hydroxide, for example sodium or potassium hydroxide and is, preferably, the mono- or disodium salt.

Other pharmaceutically acceptable salts are formed by reaction with amines such as trimethyl-, ethyl-, diethyl-, or triethylamine, piperidine, piperazine, 2-hydroxyethylpiperazine, cyclohexylamine, pyrrolidine, or choline.

In the synthetic phospholipid (I) $R_1$ and $R_2$ preferably are straight chained alkenoyl with an even number from 10 to 20 carbon atoms, for example 9-cis-dodecenoyl, 9-cis-tetradecenoyl, 9-cis-hexadecenoyl, 6-cis-, 6-trans-, 9-cis-, 9-trans-, or 11-cis-octadecenoyl, or 9-cis-icosenoyl, X is $C_2$–$C_4$-alkylene, for example 1,2-ethylene or 1,3-propylene, or $C_2$–$C_4$-alkenylene, for example vinylene.

Most preferred are the sodium or disodium salts of N-[1,2-di-(9-cis-octadecenoyl)-sn-glycero-3-phosphoethanol]-N-hydroxysuccinylamine and N-[1,2-di-(9-cis-octadecenoyl)-sn-glycero-3-phosphoethanol]-N-hydroxyglutarylamine.

In the phospholipid of the formula II (component b) the acyl groups $R_3$ and $R_4$ are preferably straight chained with an even number from 10–20 carbon atoms, for example $C_{10}$–$C_{20}$-alkanoyl or $C_{10}$–$C_{20}$-alkenoyl, especially 9-cis-dodecenoyl, 9-cis-tetradecenoyl, 9-cis-hexadecenoyl, 6-cis-, 6-trans-, 9-cis-, 9-trans-, or 11-cis-octadecenoyl.

Most preferred is 1,2-di-(9-cis-octadecenoyl)-sn-glycero-3-phosphoethanolamine. Compounds or mixtures of compounds having pharmacological activity (component c) are preferably drugs selected from the group consisting of antiphlogistics and/or antiinflammatory agents, antibiotics, antileishmaniasis agents, antimycotics, antineoplastic agents, and compounds having immunomodulatory action.

Antiphlogistics and/or antiinflammatory agents are preferably glucocorticoids, for example cortisone, hydrocortisone, prednisone, prednisolone, fluocortolone, triamcinolone, methylprednisolone, prednylidene, paramethasone, dexamethasone, betamethasone, beclomethasone, fluprednylidene, desoximethasone, fluocinolone, flumethasone, diflucortolone, clocortolone, clobetazol, or fluorcortinebutylester, salts of substituted phenylacetic acids or 2-phenylpropionic acids, for example alclofenac, ibufenac, ibuprofen, clindanac, fenclorac, ketoprofen, fenoprofen, indoprofen, fenclofenac, dichlofenac, flurbiprofen, pirprofen, naproxen, benoxaprofen, carprofen or cicloprofen; analgesically active anthranilic acid derivatives, for example of the formula

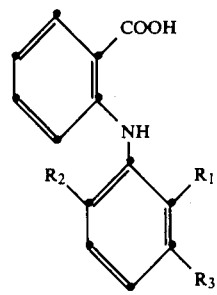

in which $R_1$, $R_2$ and $R_3$, independently of each other, represent hydrogen, methyl, chlorine or trifluoromethyl, for example mefenamic acid, flufenamic acid, tolfenamic acid or meclofenamic acid; analgesically active anilino-substituted nicotinic acid derivatives, for example miflumic acid, chlonixin or flunixin; analgesically active heteroarylacetic acids or 2-heteroarylpropionic acids having a 2-indol-3-yl or pyrrol-2-yl radical, for example indomethacin, oxmetacin, intrazol, acemetazin, cinmetacin, zomepirac, tolmetin, colpirac or tiaprofenic acid, analgesically active indenylacetic acids, for example sulindac, analgesically active heteroaryloxyacetic acids, for example benzadac.

Antibiotics are preferably tetracycline derivatives of the formula:

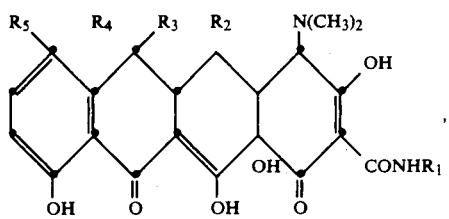

in which $R_1$ represents hydrogen or pyrrolidin-1-ylmethyl, $R_2$ represents hydrogen or hydroxy, $R_3$ represents hydrogen, hydroxy or methyl, $R_4$ represents hydrogen or methyl, and $R_5$ represents hydrogen, chlorine or dimethylamino, for example chlorotetracycline, oxytetracycline, tetracycline, demethylchlortetracycline, metacycline, doxycycline, minocycline or rolitetracycline, aminoglycosides, for example kanamycin, amikacin, gentamicin $C_1$, $C_{1a}$, $C_2$ or $C_{2b}$, sisomicin, netilmicin, spectinomycin, streptomycin, tobramycin, neomycin B, dibecacin, or kanendomycin, makrolides, for example maridomycin or erythromycin, lincomycins, for example clindamycin or lincomycin, penicillanic acid and cephalosporanic acid derivatives having antibiotic activity with 6β- or 7β-acylamino groups, which are present in fermentatively, semi-synthetically or synthetically obtainable 6β-acylaminopenicillanic acid or 7β-acylaminocephalosporanic acid derivatives or in 7β-acylaminocephalosporanic acid derivatives modified in the 3-position, for example penicillanic acid derivatives that have become known under the names penicillin G or V, phenethicillin, propicillin, nafcillin, oxacillin, cloxacillin, dicloxacillin, flucloxacillin, cyclacillin, epicillin, mecillinam, methicillin, azlocillin, sulbenicillin, ticarcillin, mezlocillin, piperacillin, carindacillin, azidocillin or ciclazillin, or cephalosporin derivatives that have become known under the names cefaclor, cefuroxime, cefazlur, cephacetrile, cefazolin, cephalexin, cefadroxil, cephaloglycin, cefoxitin, cephaloridine, cephsulodin, cefotiam, ceftazidine, cefonicid, cefotaxime, cefmenoxime, ceftizoxime, cephalothin, cephradine, cefamandol, cephanone, cephapirin, cefroxadin, cefatrizine, cefazedone, ceftrixon or ceforanid, other β-lactam antibodies of the clavam; penem or carbapenem type, for example moxalactam, clavulanic acid, nocardicine A, sulbactam, aztreonam or thienamycine, or other antibiotics of the bicomycin, novobiocin, chlor- or thiamphenicol, rifampicin-, fosfomycin-, colistin- or vancomycin type.

Antileishmaniasis agents preferably are antimony compounds, for example potassium antimonyl tartrate, stibophen, sodium stibocaptate, or sodium stibogluconate.

Antimycotics are, for example, thiocarbonic acid derivatives, for example dibenzthione, tolnaftate, or tolcidate, imidazole derivatives, for example clotrimazole, miconazole, econazole, iconazole, or ketoconazole, or polyene derivatives such as nystatine, natamycine, or amphotericine B.

Antineoplastic agents preferably are alkylating agents having the bis-(2-chloroethyl)-amine group such as chlormethine, chlorambucile, melphalan, uramustine, mannomustine, extramustinephosphat, mechlorethaminoxide, cyclophosphamide, ifosfamide, or trifosfamide, alkylating agents having a substituted aziridine group, for example tretamine, thiotepa, triaziquone, or mitomycine, alkylating agents of the methanesulfonic ester type such as busulfane, alkylating N-alkyl-N-nitrosourea derivatives, for example carmustine, lomustine, semustine, or streptozotocine, alkylating agents of the mitobronitole, dacarbazine, or procarbazine type, complexing agents such as cis-platin, antimetabolites of the folic acid type, for example methotrexate, purine derivatives such as mercaptopurine, thioguanine, azathioprine, tiamiprine, vidarabine, or puromycine, pyrimidine derivatives, for example fluorouracil, floxuridine, tegafur, cytarabine, idoxuridine, flucytosine, antibiotics such as dactinomycin, daunorubicin, doxorubicin, mithramycin, bleomycin $A_2$ or $B_2$ or etoposide, or vinca alcaloids, optionally in combination with chlormethamine, prednisolone, prednisone, or procarbazine.

Compounds or mixtures of compounds having immunomodulatory action are, for example, muramylpeptides of the formula

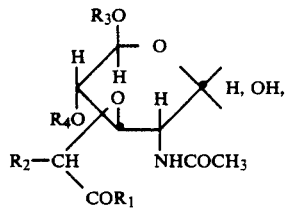

(V)

wherein $R_1$ represents the L-Ala-D-isoGln-L-Ala-2-(1,2-dipalmitoyl-sn-glycero-3-hydroxyphosphoryloxy)-ethylamide, L-Ala-D-Glu-($C_{gamma}$)-L-Ala-2-(1,2-dipalmitoyl-sn-glycero-3-hydroxyphosphoryloxy)-ethylamide, L-Ala-D-isoGln-OH, L-Ala-D-Gln-$NH_2$-α-n-butylester, L-Ala-D-isoGln-L-(stearoyl)-Lys, L-Val-D-Gln-$NH_2$-α-n-methylester, L-Ala-D-isoGln-L-Ala-1,2-dipalmitoyl-sn-glycerineester or the L-Ala-D-isoGln-L-Ala-cholesterineester group, $R_2$ represents hydrogen, methyl or n-propyl, $R_3$ represents hydrogen, n-stearoyl, 10-(2,3-dimethoxy-1,4-dioxo-5-methyl)-2,5-cyclohexadienoyl, 2-behenoyloxy-2-methyl-propanoyl or n-octanoyl, and $R_4$ represents hydrogen or n-octanoyl, as well as the 2-palmitoylthio derivative thereof, lipopeptides such as n-lauroyl-L-Ala-D-isoGln-(m-DAP-Gly)-$NH_2$, n-lauroyl-L-Ala-D-isoGln-(L-DAP-Gly)-$NH_2$, n-lauroyl-L-Ala-D-isoGln-(L-Lys-D-Ala)-$NH_2$, n-octanoyl-L-Ala-D-isoGln-(L-Lys-D-Ala)-$NH_2$ or palmitoyl-Cys-((2R)-2,3-dilauroyloxy-propyl)-Ala-D-Glu-(Gly-taurine-Na)-$NH_2$, or are lymphokines which are produced by lymphocytes, monocytes or macrophages after stimulation by antigenes or mitogenes.

Lymphokines are especially gamma interferon, especially natural or recombinant human gamma interferon, especially human gamma-interferon obtainable according to the European Patent Applications Nos. 63,482, 77,670, 83,777, 88,540, 89,676, 95,350, 99,084, 110,044 and 112,967 and the International (PCT) Applications (WO) No. 83/04,053 or WO No. 84/02,129 or as desirbed in U.S. Pat. Nos. 4,376,821; 4,727,138; 4,532.001 and 4,582,800.

Preferred is human gamma-interferon of the following amino acid sequences:

$H_2N$—Cys—Tyr—Cys—Gln—Asp—Pro—Tyr—Val—Gln—Glu—Ala—Glu—Asn—Leu—Lys—Lys—Tyr—Phe—Asn—Ala—Gly—His—Ser—Asp—Val—Ala—Asp—Asn—Gly—Thr—Leu—Phe—Leu—Gly—Ile—Leu—Lys—Asn—Trp—Lys—Glu—Glu—Ser—Asp—Arg—Lys—Ile—Met—Gln—Ser—Gln—Ile—Val—Ser—Phe—Tyr—Phe—Lys—Leu—Phe—Lys—Asn—Phe—Lys—Asp—Asp—Gln—Ser—Ile—Gln—Lys—Ser—Val—Glu—Thr—Ile—Lys—Glu—Asp—Met—Asn—Val—Lys—Phe—Phe—Asn—Ser—Asn—Lys—Lys—Lys—Arg—Asp—Asp—Phe—Glu—Lys—Leu—Thr—Asn—Tyr—Ser—Val—Thr—Asp—Leu—Asn—Val—Gln—Arg—Lys—Ala—Ile—His—Glu—Leu—Ile—Gln—Val—Met—Ala—Glu—Leu—Ser—Pro—Ala—Ala—Lys—Thr—Glu—Lys—Arg—Lys—Arg—Ser—Gln—Met—Leu—Phe—Gln—Gly—Arg—Arg—Ala—Ser—Gln—OH, and $H_2N$—Cys—Tyr—Cys—Gln—Asp—Pro—Tyr—Val—Lys—Glu—Ala—Glu—Asn—Leu—Lys—Lys—Tyr—Phe—Asn—Ala—Gly—His—Ser—Asp—Val—Ala—Asp—Asn—Gly—Thr—Leu—Phe—Leu—Gly—Ile—Leu—Lys—Asn—Trp—Lys—Glu—Glu—Ser—Asp—Arg—Lys—Ile—Met—Gln—Ser—Gln—Ile—Val—Ser—Phe—Tyr—Phe—Lys—Leu—Phe—Lys—Asn—Phe—Lys—Asp—Asp—Gln—Ser—Ile—Gln—Lys—Ser—Val—Glu—Thr—Ile—Lys—Glu—Asp—Met—Asn—Val—Lys—Phe—Phe—Asn—Ser—Asn—Lys—Lys—Lys—Arg—Asp—Asp—Phe—Glu—Lys—Leu—Thr—Asn—Tyr—Ser—Val—Thr—Asp—Leu—Asn—Val—Gln—Arg—Lys—Ala—Ile—His—Glu—Leu—Ile—Gln—Val—Met—Ala—Glu—Leu—Ser—Pro—Ala—Ala—Lys—Thr—Gly—Lys—Arg—Lys—Arg—Ser—Gln—Met—Leu—Phe—Arg—Gly—Arg—Arg—Ala—Ser—Gln—OH, human interleukine 2 obtainable, for example, from the culture filtrates of cell cultures of leukaemia or lymphoma cells after activation or stimulation with human T-cell mitogenes and by purification with reverse phase HPLC, culture filtrates that contain mixtures of compounds known as migration inhibition factor (MIF), leukocytes migration inhibition factor, macrophages activating factor (MAF), colony stimulating factor, as well as interleukine 1 and 2 and gamma interferon and which are obtained from cultures of human T-lymphocytes from the spleen or from peripheral blood after stimulation by antigenes or mitogenes, or example human T-cell leukaemia-lymphoma virus (HTLV I or II), phytohaemagglutinine, or concanavaline, especially those culture filtrates or isolates that contain a high percentage of macrophage activating factor (MAF).

Preferred are N-acetylmuramyl-L-alanyl-D-isoglutaminyl-L-alanine-2-(1,2-dipalmitoyl-sn-glycero-3-hydroxyphosphoryloxy)-ethylamide, sodium-N-acetyl- D-muramyl-L-alanyl-D-isoglutamine or sodium-N-acetyldesmethylmuramyl-L-alanyl-D-isoglutamine of the formula V, optionally in combination with purified, natural or recombinant human gamma interferon.

Lipids (component d) selected from the group consisting of phosphatidylchloline, phosphatidylserine, phosphatidylinositol, phosphatidylglycerol and cardiolipin, are synthetic phospholipids or are mixtures of phospholipids having various acyl groups of different molecular weight and structure, for example soy bean or chicken egg phosphatidylcholine or phosphatidylcholine from bovine brain, bovine liver or porcine liver, phosphatidylserine from bovine brain, phosphatidylinositol from soybean or from yeast, phosphatidylglycerol from egg yolk, or cardiolipin from bovine heart.

Derivatives of cholesterol are for example, cholestane, coprostane, ergosterol or stigmasterol.

The pharmaceutical compositions according to the present invention, when applied in the form of liposomes, are characterized by their excellent phagocytosis. For example, phagocytosis of multilamellar liposomes consisting of a 3:7 molar mixture of sodium-N-[1,2-di-(9-cis-octadecenoyl)-sn-glycero-3-phospoethanol]-N-hydroxysuccinylamine (I) and dioleoylphosphatidylethanolamine (II) or sodium-N-[1,2-di-(9-cis-octadecenoyl)-sn-glycero-3-phosphoethanol]-N-hydroxyglutarylamine (I) and phosphatidylethanolamine (II) by mouse peritoneal macrophages is higher than phagocytosis of multilamellar liposomes consisting exclusively of phosphatidylethanolamine or of a 3:7 molar mixture of phosphatidylserine and phosphatidylcholine. This can be demonstrated in-vitro by incubation of mouse peritoneal macrophages with multilamellar liposomes containing trace amounts of $^{125}$I as a liposome marker. At regular intervals the cultures are washed and the amount of cell-associated radiation is determined. Moreover, liposomes consisting of phospholipids of formula I and II in a molar ration of 3:7 containing immunomodulators such as MDP and gamma interferon show higher activation of macrophages to the tumoricidal state at low doses than liposomes consisting of phophatidyl choline and phosphatidyl serine containing the same amount of MDP and gamma-interferon. This can also be shown in vitro by plating peritoneal mouse macrophages in culture wells and activating the macrophages with multilamellar liposomes consisting of sodium-N-[1,2-di-(9-cis-octadecenoyl)-sn-glycero-3-phosphoethanol]-N-hydroxysuccinylamine (I) and dioleoylphosphatidylethanolamine (II) in a molar 3:7 ratio containing MDP and gamma interferon and with multilamellar liposomes consisting of phosphatidylcholine and phosphatidylserine in the same molar ratio containing MDP and gamma interferon. The liposome preparations are used at a concentration of 100 nmol of total phospholipid per well and contains 6 units recombinant immune gamma interferon and 0.2 g MDP. After washing the wells $10^4$[$^{125}$I]iododeoxyuridine - labeled BL6 melanoma cells are added. Cytotoxicity is determined after 72 hours of cocultivation by measuring the radioactivity associated with the adherent viable target cells after washing the cultures three times with Hank's balanced salt solution. Percent cytotoxicity can be calculated with respect to the counts per minute in control cultures containing unactivated macrophages and target cells.

The pharmaceutical compositions according to the present invention, when applied in the form of liposomes, are also characterized by their excellent release properties at low pH-values. The release properties of liposomes consisting of disodium-N-[1,2-di-(9-cis-octadecenoyl)-sn-glycero-3-phosphoethanol]-N-hydroxysuccinylamine and 1,2-di-(9-cis-octadecenoyl)-sn-glycero-3-phosphoethanolamine in a molar ratio of 3:7 are analyzed according to the fluorescence method to measure the leakage from liposomes at low pH-values as described by Ellens et al. Biochemistry 1984, 23, 1532–1538. To investigate the pH dependence of leakage, liposomes are injected into buffer solutions ranging from pH 4.0 to 7.4 and the percentage of the entrapped 8-aminonaphthalene-1,3,6-trisulfonic acid (ANTS) and p-xylylene-bis-pyridinium dibromide (DPX) which replace the encapsuled pharmaceutical in this assay, is determined. Complete encapsulation of the water soluble fluorophore ANTS complexed with the "quencher" DPX extinguishes most of the ANTS fluorescence. Leakage of ANTS from the liposomes could be followed by the increase in fluorescence due to the relief of DPX "quenching".

It has now been found that there is essentially no leakage above pH 6.0. However, when the pH is decreased, there is a concomitant enhancement in the amount of ANTS/DPX release from the liposomes with half maximal release occurring at approximately pH 4.5 and complete release at about 4.0.

It is known that pathologic tissues have an ambient pH that is considerably lower than that of normal tissues. For example of primary tumors, metastasis, inflammation, and infection have reduced local pH-environments. The liposomes of the present invention, therefore, would deliver their content, for example antiinflammatory drugs or immunomodulators specifically to the site of inflammation, the primary tumor or metastasis and release these drugs in the acidic environment of these pathologic tissues. For example, liposomes consisting of a 3:7 molar mixture of disodium-N-[1,2-di-(9-cis-octadecenoyl)-sn-glycero-3-phosphoethanol]-N-hydroxysuccinylamine (I) and dioleoylphosphatidylethanolamine release more of their content, for example an effective dose of recombinant human gamma interferon, at low pH values, e.g. pH 4, than at higher or neutral pH values. This can be shown in-vitro in buffer solutions of pH 7.4 and pH 4 by determining at regular time intervals the radiation of marked $^{125}$I-Interferon released from the lipids. For example, at a pH-value of about 4 more than 25% of enclosed gamma-interferon are released from liposomes after 180 minutes.

Therefore, the pharmaceutical compositions according to the present invention, when applied in the form of liposomes, are excellent administration systems for drug delivery to the reduced local pH environment of pathologic tissues. Therefore, they are especially useful in the cancer chemotherapy for combating metastatic tumor cells.

Aqueous liposome dispersions wherein the phospholipids of the formulae I and II are the encapsulating material and compounds or a mixture of compounds having pharmacologic activity are encapsulated, optionally after concentration or isolation of the liposomes, for example in the (ultra) centrifuge, are suitable for therapeutic purposes for parenteral (bukkal, lingual, sublingual, i.v., i.c., topical, s.c., i.m. or nasal) administration.

For parenteral administration (topical) the liposome-containing aqueous dispersion can be mixed with customary thickeners, for example hydroxypropylmethylcellulose, suitable preservatives, antioxidants and perfumes, and can be used in the form of a lotion or a gel for application to the skin or mucous membranes.

For parenteral administration, the aqueous dispersion of the enriched liposomes can be suspended in a suitable carrier liquid, for example sterile, calcium free, isotonic sodium chloride or glucose solution, optionally buffered to pH 7.2–7.4.

The dosage of the active ingredient to be administered is generally the highest and lowest dose amount as prescribed, for example in the Deutsches Arzneimittelbuch (DAB) [German Pharmacopoieia] for the specific active ingredient for the particular form of administration, the age of the patient and the health of the patient. Aqueous liposome dispersions also have the advantage, however, that active ingredients administered in smaller doses may, nevertheless, pass to the receptors and produce a therapeutic effect, or, on administration of higher doses, undesirable side effects may be avoided.

The preferred dosage amount for the liposome encapsulated immunomodulators of the muramylpeptide or lipopeptide type is about 0.001 up to 10 mg/kg body weight per dose. For human gamma interferon or mixtures containing MAF the preferred dosage amount is about 0.01 ml liposome dispersion per kilo body weight containing 100–1000 units of gamma interferon or MAF. If muramylpeptides are administered in combination with gamma interferon, it is estimated that the highest dose to be applied to a human of about 70 kg weight is about 10 mg of liposomes per kilo body weight containing 3 micrograms of the muramylpeptide and 1500 units of gamma interferon. The highest and the lowest dose of the encapsulated material, the concentration of the phospholipids in the aqueous phase as well as the concentration of the encapsulated compounds can be varied according to results to be established experimentally in clinical trials.

The present invention preferably relates to pharmaceutical compositions consisting of (a) a phospholipid of the formula I, wherein m represents two, $R_1$ and $R_2$ are defined as above, X represents $C_1$–$C_4$-alkylene, $C_2$–$C_4$-alkenylene or $C_1$–$C_4$-alkylene substituted by hydroxy or a pharmaceutically acceptable salt thereof, (b) a phospholipid of the formula II, wherein $R_3$ and $R_4$ independently of each other represent straight chained $C_{10}$–$C_{20}$-alkanoyl or $C_{10}$–$C_{20}$-alkenoyl, (c) a compound or a combination of compounds having pharmacological activity, and, optionally, a pharmaceutically acceptable carrier solution buffered to pH 7.2–7.4.

More preferably, the present invention relates to pharmaceutical compositions consisting of (a) a phospholipid of the formula I, wherein m represents two, $R_1$ and $R_2$ are defined as above, X represents $C_2$–$C_4$-alkylene or $C_2$–$C_4$-alkenylene, or a pharmaceutically acceptable salt thereof, (b) a phospholipid of the formula II, wherein $R_3$ and $R_4$ independently of each other represent straight chained $C_{10}$–$C_{20}$-alkanoyl or $C_{10}$–$C_{20}$-alkenoyl, (c) a compound or a combination of compounds selected from the group consisting of antiphlogistics and/or antiinflammatory agents, antibiotics, antileishmaniasis agents, antineoplastic agents and immunomodulators and, optionally, a pharmaceutically acceptable carrier solution buffered to pH 7.2–7.4.

The present invention specifically relates to pharmaceutical compositions consisting of (a) a phospholipid of the formula I, wherein m represents two, $R_1$ and $R_2$ independently of each other represent straight chained alkanoyl or alkenoyl with an even number from 10 to 20 carbon atoms, X represents $C_2$–$C_4$-alkylene, for example 1,2-ethylene or 1,3-propylene, or $C_2$–$C_4$-alkenylene, for example vinylene, or a pharmaceutically acceptable salt thereof, (b) a phospholipid of the formula II, wherein $R_3$ and $R_4$ represent straight chained $C_{10}$–$C_{20}$-alkenoyl with an even number from 10 to 20 carbon atoms, (c) a compound or a combination of compounds selected from the group consisting of antiphlogistics and/or antiinflammatory agents, antibiotics, antineoplastic agents and immunomodulators and, optionally, a pharmaceutically acceptable carrier solution buffered to pH 7.2–7.4.

The invention more specifically relates to pharmaceutical compositions consisting of (a) a phospholipid of the formula I, wherein m represents two, $R_1$ and $R_2$ independently of each other represent 9-cis-dodecenoyl, 9-cis-tetradecenoyl, 9-cis-hexadecenoyl, 6-cis-, 6-trans-, 9-cis-, 9-trans-, or 11-cis-octadecenoyl, or 9-cis-icosenoyl, X represents $C_2$–$C_4$-alkylene, for example 1,2-ethylene or 1,3-propylene, or $C_2$–$C_4$-alkenylene, for example vinylene, or a pharmaceutically acceptable salt thereof, (b) a phospholipid of the formula II, wherein $R_3$ and $R_4$ independently of each other represent 9-cis-dodecenoyl, 9-cis-tetradecenoyl, 9-cis-hexadecenoyl, 6-cis-, 6-trans-, 9-cis-, 9-trans-, or 11-cis-octadecenoyl, or 9-cis-icosenoyl, (c) a compound or a combination of compounds selected from the group consisting of antiphlogistics and/or antiinflammatory agents, antibiotics, antineoplastic agents and immunomodulators, and, optionally, a pharmaceutically acceptable carrier solution buffered to pH 7.2–7.4.

Especially, the present invention relates to pharmaceutical compositions consisting of (a) sodium or disodium-N-[1,2-di-(9-cis-octadecenoyl)-sn-glycero-3-phosphoethanol]-N-hydroxysuccinylamine or sodium or disodium-N-[1,2-di-(9-cis-octadecenoyl)-sn-glycero-3-phosphoethanol]-N-hydroxyglutarylamine, (b) 1,2-di-(9-cis-octadecenoyl)-sn-glycero-3-phosphoethanolamine, (c) a compound or a combination of compounds selected from the group consisting of antiphlogistic and/or antiinflammatory agents, antibiotics, antineoplastic agents, and immunomodulators, and, optionally, a pharmaceutically acceptable carrier solution buffered to pH 7.2–7.4.

Of high preference are pharmaceutical compositions consisting of (a) sodium or disodium-N-[1,2-di-(9-cis-octadecenoyl)-sn-glycero-3-phosphoethanol]-N-hydroxysuccinylamine or sodium or disodium-N-[1,2-di-(9-cis-octadecenoyl)-sn-glycero-3-phosphoethanol]-N-hydroxyglutarylamine, (b) 1,2-di-(9-cis-octadecenoyl)-sn-glycero-3-phosphoethanolamine, (c) a compound or a combination of compounds selected from the group consisting of diclofenac, pirprofen, mitomycin, cytarabine, dactinomycin, daunorubicin, doxorubicine, etoposide, N-acetylmuramyl-L-alanyl-D-isoglutaminyl-L-alanine-2-(1,2-dipalmitoyl-sn-glycero-3-hydroxyphosphoryloxy)-ethylamide, N-acetylmuramyl-L-alanyl-D-glutamic acid-(C$\gamma$-

L-alanine-2-(1,2-dipalmitoyl-sn-glycero-3-hydroxyphosphoryloxy)-ethylamide-disodium salt, N-acetylmuramyl-L-alanyl-D-isoglutamine-sodium salt, N-acetyldesmethyl-muramyl-L-alanyl-D-isoglutamine-sodium salt, N-acetylmuramyl-L-alanyl-D-glutamine-α-n-butylester, N$^\alpha$-(N-acetylmuramyl-L-alanyl-D-isoglutaminyl)-N$^\gamma$-stearoyl-L-lysine, 6-O-stearoyl-N-acetylmuramyl-L-alanine-D-isoglutamine and lymphokines, and, optionally, a pharmaceutically acceptable carrier solution buffered to pH 7.2–7.4.

Especially preferred are pharmaceutical compositions consisting of (a) sodium or disodium-N-[1,2-di-(9-cis-octadecenoyl)-sn-glycero-3-phosphoethanol]-N-hydroxysuccinylamine or sodium or disodium-N-[1,2-di-(9-cis-octadecenoyl)-sn-glycero-3-phosphoethanol]-N-hydroxyglutarylamine, (b) 1,2-di-(9-cis-octadecenoyl)-sn-glycero-3-phosphoethanolamine, (c) a compound or a combination of compounds of the group consisting of diclofenac, pirprofen, mitomycin, cytarabine, dactinomycin, daunorubicin, doxorubicine, etoposide, N-acetylmuramyl-L-alanyl-D-isoglutaminyl-L-alanine-2-(1,2-dipalmitoyl-sn-glycero-3-hydroxyphosphoryloxy)-ethylamide, sodium-N-acetyl-muramyl-L-alanyl-D-isoglutamine, sodium-N-acetyldesmethyl-muramyl-L-alanyl-D-isoglutamine, purified, natural or recombinant human gamma interferon, interleukine 2, and compounds obtained from cultures of human T-lymphocytes from the spleen or from peripheral blood after stimulation by antigenes or mitogenes and which are characterized by a high percentage of macrophage activating factor (MAF), and, optionally, a pharmaceutically acceptable carrier solution buffered to pH 7.2–7.4.

Most preferred are pharmaceutical compositions consisting of (a) sodium or disodium-N-[1,2-di-(9-cis-octadecenoyl)-sn-glycero-3-phospho-ethanol]-N-hydroxysuccinylamine or sodium or disodium-N-[1,2-di-(9-cis-octadecenoyl)-sn-glycero-3-phosphoethanol]-N-hydroxyglutarylamine, (b) 1,2-di-(9-cis-octadecenoyl)-sn-glycero-3-phosphoethanolamine, (c) a compound or a combination of compounds consisting of N-acetylmuramyl-L-alanyl-D-isoglutaminyl-L-alanine-2-(1,2-dipalmitoyl-sn-hydroxyphosphoryloxy)-ethylamide, sodium-N-acetyl-muramyl-L-alanyl-D-isoglutamine, sodium-N-acetyldesmethylmuramyl-L-alanyl-D-glutamine, and purified, natural or recombinant human gamma interferon, and, optionally, a pharmaceutically acceptable carrier solution buffered to pH 7.2–7.4.

The invention also relates to mixtures of synthetic phospholipids of the formulae I and II and, optionally, a lipid selected from the group consisting of phosphatidylcholine, phosphatidylserine, phosphatidylinositol, phosphatidylglycerol, cardiolipin, and, optionally, cholesterol and its derivatives, especially mixtures wherein the ratio of the phospholipid (I) to the phospholipid (II) is from about 10 to 90 to about 50 to 50 mole per cent. The ratio of 30 to 70 mole per cent is especially preferred. The mixtures are useful for preparing liposomes in an aqueous phase containing the component (c) compounds or a combination of compounds having pharmacological activity.

The invention also relates to a process for the preparation of the pharmaceutical compositions mentioned above or of the mixture mentioned above, characterized in that (a) a homogeneous mixture consisting of phospholipids of the formulae I and II, a lipophilic compound or mixture of compounds having pharmacological activity and, optionally, a lipid mentioned above from natural sources is prepared and, optionally, the homogeneous mixture thus obtained is dispersed in an aqueous phase or, (b) a homogeneous mixture consisting of phospholipids of the formulae I and II and, optionally, a lipid mentioned above from natural sources is prepared and, optionally, the homogeneous mixture thus obtained is dispersed in an aqueous phase containing a hydrophilic compound or mixture of compounds having pharmacological activity and, if necessary, the aqueous dispersion thus obtained is buffered to pH 7.0–7.8 and, if desired, non-encapsulated lipids and/or compounds having pharmacological activity are separated from the aqueous phase and/or the liposomes thus obtained are concentrated or separated off from the aqueous phase.

The homogenous mixture is prepared by formation of a film or of a lyophilisate.

The film is prepared according to method (a) by dissolving the phospholipids (I) and (II) and the lipophilic compound or mixture of compounds and, optionally, a lipid mentioned above from natural sources or according to method (b) by dissolving the phospholipids (I) and (II) and, optionally, a lipid mentioned above from natural sources in an organic solvent and stripping the solvent.

Suitable solvents are, for example, unsubstituted or substituted, for example halogenated, aliphatic or cycloaliphatic hydrocarbons, for example n-hexane, cyclohexane, methylenechloride, or chloroform, alcohols, for example methanol or ethanol, lower alkanecarboxylic acid esters or amides, for example acetic acid ethylester or dimethylformamide, or ethers, for example diethylether, tetrahydrofurane or dioxane, or mixtures of these solvents. The organic solvent is subsequently stripped by applying a vacuum, preferably a high vacuum, or by blowing off with an inert gas, for example nitrogen.

The lyophilisate is formed according to method (a) by dissolving the phospholipids (I) and (II) and the lipophilic compounds or mixture of compounds or according to method (b) by dissolving the phospholipids (I) and (II) in an organic solvent according to the method as described in the U.S. Pat. No. 4,311,712. Suitable solvents are in the solid form together with the phospholipids (I) and (II) at the temperature of the lyophilisation process and are having a melting point of more than 0° C., for example glacial acetic acid, benzene or dioxane, especially tert-butanol.

A homogeneous mixture may also be prepared by spray-drying a solution of the phospholipids (I) and (II) and of the encapsulating material in an organic solvent having a low boiling point such as chloroform. A powder is obtained by this method.

The ratio of the phospholipid component (I) to the phospholipid component (II) in the homogenous mixture is approximately 10 v. 90 up to 50 v. 50 mole per cent. Preferred is the ratio 30 v. 70 mole per cent. The approximate ratio of the molar amounts of the encapsulated material (gamma-interferon) divided by the total amount of the phospholipids (I) and (II) is about 0.0001 to 0.1 v. 1.0, preferably 0.005 to 0.01 v. 0.1.

The dispersion is carried out by mechanical agitation (shaking, stirring, Vortex mixer) the aqueous phase to which according to method (a) the homogenous mixture of the phospholipids (I) and (II) and the lipophilic compounds or the lipophilic mixture of compounds having pharmacological activity have been added. According to method (b) the aqueous phase containing the hydrophilic compounds or mixture of compounds having pharmacological properties is added to the homogeneous mixture of the phospholipids (I) and (II).

A mixture of small, large, unilamellar or multilamellar liposomes is formed spontaneously at a high rate without supplying external energy. Approximately 0.1 to 40 per cent per weight, preferably 2 to 20 per cent per weight, of the homogeneous mixture relative to the total weight of the aqueous dispersion can be dispersed in the aqueous phase. Such dispersions can further be diluted to about 1 micromole lipid per ml. Such liposome dispersions have entrapped approximately 2.5 microliters of the aqueous phase per micromole of the lipid.

Acidic or basic aqueous dispersions are buffered to approximately pH 7.0–7.8, preferably 7.2–7.4. Preferably, the dispersion is carried out in an aqueous phase having a pH from 7.2 to 7.4.

Method (a) is preferred in the event that lipophilic, water insoluble compounds are encapsulated in liposomes, for example lipophilic muramyltripeptides.

Method (b) is preferred in the event that hydrophilic water insoluble compounds are encapsulated in liposomes, for example cytarabine or cytostatic compounds such as trifosfamide.

The preparation of the pharmaceutical compositions according to the present invention in the form of liposomes can also be carried out by other methods known in the art for preparing liposomes, for example by sonication with ultrasonic waves, by infusion methods or reversed phase evaporation.

The dispersion step is performed at temperatures below 60°, preferably at room temperature. In case of a potential thermal sensitivity of the encapsulated material, the dispersion is carried out under cooling and, optionally, under inert gas atmosphere, for example nitrogen or argon atmosphere.

The liposomes obtained can be made storage stable in the aqueous phase up to several weeks or months after addition of stabilizers, for example mannite or lactose.

The size of the liposomes formed depends, inter alia, on the structure of the active ingredient and the lipid component, the mixing ratio of the components and the concentration of these components in the aqueous dispersion. Thus, for example, by increasing or reducing the concentration of the lipid components aqueous phases having a high content of small or large liposomes are produced.

The separation of small liposomes from large liposomes is effected by means of conventional separation methods, for example sedimentation of the large liposomes in an ultracentrifuge, by gel filtration or extrusion through straight-pored filters. For example, on centrifuging, for example from 5 to 60 minutes in a rotational field giving rise to an inertial force equivalent to a gravitational field of 5000–40,000× g, large liposomes are deposited at the bottom of the vessel, whilst small liposomes remain dispersed and can be decanted off. After repeated centrifugation, complete separation of large liposomes from small liposomes is achieved. Preferably, liposomes are separated from the aqueous phase in the event that according to method (b) the aqueous phase contains non-encapsulated water insoluble compounds or pharmaceuticals. Especially, water soluble antineoplastic agents, for example alkylating agents such as cyclofosfamide, should be separated off by filtration, ultrafiltration, dialysis or by centrifugation in order to prevent eventual side effects caused by non-encapsulated compounds. The liposome fraction can be admixed with a carrier solution buffered to pH 7.2–7.4, for example isotonic, sterile sodium chloride solution buffered to pH 7.2–7.4.

Liposomes in the aqueous phase having a diameter greater than $6.0 \times 10^{-8}$ m, for example large multilamellar liposomes, can be separated off by gel filtration, for example with Sepharose or Sephacryl as carriers.

By extrusion through straight-pored filters, for example membrane filters of the Acrodisc®, Nucleopore® or polycarbonate type having a pore diameter of approximately $1.0 \times 10^{-6}$–$1.0 \times 10^{-8}$ m at a pressure of approximately from 0.1 to 1.5 bar and a filtration rate of approximately 20 ml/h, a particularly uniform size distribution of the liposomes is obtained.

The formation of liposomes and their content in the aqueous phase can be detected in a manner known per se by using various physical analytical methods, for example by microscopy of freeze-fracture samples and thin sections in an electron microscope, by X-ray refraction, by dynamic light scattering, by mass determination of the filtrate in an analytical ultracentrifuge and, especially, by spectroscopy, for example in the nuclear magnetic resonance spectrum ($^1$H, $^{13}$C and $^{31}$P).

Synthetic phospholipids of the formula I are known. Their preparation as intermediates has been described in the U.S. Pat. No. 4,423,038.

The phospholipids of the formula II are all known. Some of them are commercially available (Avanti, Fluka, Serva, Sigma).

The pharmaceuticals mentioned above, especially the antiphlogistic, antirheumatic, antileishmaniasis agents, antimycotics, antibiotics or antineoplastic agents are all known, see, for example, MERCK Index, Tenth Edition.

The preparation of muramylpeptides of Formula V is described in U.S. Pat. Nos. 4,406,890 and 4,317,771. Immunomodulators of the lipopeptide type are described in U.S. Pat. No. 4,675,180. The preparation of purified, natural, and recombinant gamma interferon is described in U.S. Pat. Nos. 4,376,821, 4,727,138, 4,532,001, and 4,582,800. The preparation of purified interleukin 2 is described in U.S. Pat. No. 4,448,879.

The buffer solutions of pH 7.0 to 7.8 preferably are sterile phosphate buffer solutions based on the dihydrogenphosphate/hydrogenphosphate equilibrium ($KH_2PO_4/Na_2HPO_4$). The preparation of these buffer solutions is described in standard manuals, for example "Hager's Handbuch der Pharmazeutischen Praxis", Springer Verlag, Vol. 1, pg. 357–359. Especially sterile, isotonic calcium-free buffer solution of pH 7.2 (Dulbecco) or Hank's Balanced Salt Solution (M.A. Bioproducts, Walkersville Md. U.S.A.) is used.

The following examples are illustrating the invention without limiting the scope thereof. Temperatures are given in degrees Celsius.

EXAMPLE 1

(a) In a round flask 84.70 mg (0.098 mmol) disodium-N-[1,2-di-(9-cis-octadecenoyl)-sn-glycero-3-phosphoethanol]-N-hydroxysuccinylamine and 168.10 mg (0.226 mmol) 1,2-di-(9-cis-octadecenoyl)-sn-glycero-3-phosphoethanolamine are dissolved in a sufficient amount of tert-butanol until both lipids are dissolved. The solution is filtered under sterile conditions over Acrodisc ® filter ($2.0 \times 10^{-7}$ m) and is bottled in a sterile vial. This vial is frozen at $-45°$. A vacuum is applied to the frozen vial and the solvent is removed until room temperature has been reached. The vial is sealed under inert gas atmosphere, for example argon atmosphere.

To this vial containing a lyophilisate of the lipid components mentioned above, 2.5 ml of a sterile, phosphate buffered (pH 7.2–7.4), calcium free sodium chloride solution (Dulbecco) containing doxorubicin in a concentration of 4 g/l are added with a sterile syringe. The vial is then shaken for ten minutes on a standardized laboratory shaker (Vortex, speed 6) and is placed in a centrifuge. After centrifugation in a gravitational field of about $40,000 \times$ g for about 60 minutes, the supernatant is decanted. The liposome dispersion is resuspended in 2.5 ml 0.85% sterile, phosphate buffered (pH 7.2–7.4) sodium chloride solution (Dulbecco). The centrifugation and resuspension are repeated until the supernatant is free of doxorubicin. The liposome dispersion obtained is suitable for parenteral administration.

(b) Preparation of sodium-N-[1,2-di-(9-cis-octadecenoyl)-sn-glycero-3-phosphoethanol]-N-hydroxysuccinylamine 200.6 mg (270 micromol) 1,2-di-(9-cis-octadecenoyl)-sn-glycero-3-phosphoethanolamine are dried under nitrogen and placed under high vacuum for two hours. The dry lipid is dissolved in 10 ml of freshly distilled pyridine containing 54 mg (540 micromol) succinic acid anhydride. The reaction mixture is stirred for two hours under nitrogen atmosphere at 55°. The excess pyridine is removed by evaporization under reduced pressure and the excess succinic acid anhydride is hydrolyzed by suspending the residue in a mixture of chloroform-methanol-0.58% aqueous sodium chloride solution (1:2:0.8 v/v). The product is extracted by partitioning after addition of one volume chloroform and one volume 0.58% aqueous sodium chloride solution. The lower phase is washed three times with a mixture of chloroform-methanol-0.58% aqueous sodium chloride solution (3:48:47 v/v). The solvent is removed by rotary evaporation and the residue is resuspended in chloroform. Rf (Merck silicagel 60 plates): 0,375 (chloroform, methanol, water-65/25/4); UV: 254.6 nm (broad); m.p. 154° C.

EXAMPLE 2

In a manner analogous to Example 1 aqueous liposome dispersions are prepared containing 84.70 mg (0.098 mmol) disodium-N-[1,2-di-(9-cis-octadecenoyl)-sn-glycero-3-phosphoethanol]-N-hydroxy-succinylamine and 168.10 mg (0.226 mmol) 1,2-di-(9-cis-octadecenoyl)-sn-glycero-3-phosphoethanolamine and 0.1 mg up to 10 mg N-acetyl-muramyl-L-alanyl-D-isoglutamine-sodium salt or 0.1 mg up to 10 mg N-acetyl-desmethylmuramyl-L-alanyl-D-isoglutamine-sodium salt or 1000 to 100.000 units of recombinant human immune gamma-interferon obtainable according to EP-A-121,157 (Kyowa Hakko Kogyo Co.) or a combination of 1000 to 1,000,000 units of this recombinant human immune gamma-interferon with 50–200 microgramm sodium-N-acetyl-muramyl-L-alanyl-D-isoglutamine or sodium-N-acetyldesmethylmuramyl-L-alanyl-D-isoglutamine.

EXAMPLE 3

(a) In a round flask 84.70 mg (0.098 mmol) disodium-N-[1,2-di-(9-cis-octadecenoyl)-sn-glycero-3-phosphoethanol]-N-hydroxysuccinylamine and 168.10 mg (0.226 mmol) 1,2-di-(9-cis-octadecenoyl)-sn-glycero-3-phosphoethanolamine are dissolved in a sufficient amount of tert-butanol until both lipids are dissolved. The solution is filtered under sterile conditions over Acrodisc ® filter ($2.0 \times 10^{-7}$ m) and is bottled in a sterile vial. This vial is rotated at 1750 rpm (rotations per minute) and the solvent is removed in a stream of purified, filtered (at the pressure of 1 bar) dry nitrogen. The vial is evacuated in a high vacuum of $6.0 \times 10^{-2}$ mbar and is stable under argon inert gas atmosphere.

To this vial containing a thin film of the lipid components mentioned above, 2.5 ml of a sterile, phosphate buffered (pH 7.2–7.4), calcium free sodium chloride solution (Dulbecco) containing diclofenac in a concentration of 2 g/l are added with a sterile syringe. The vial is then shaken for ten minutes on a standardized laboratory shaker (Vortex, speed 6) and is placed in a centrifuge. After centrifugation in a gravitational field of about $40,000 \times$ g for about 60 minutes the supernatant is decanted. The liposome dispersion is resuspended in 2.5 ml 0.85% sterile, phosphate buffered (pH 7.2–7.4) sodium chloride solution (Dulbecco) and is suitable for parenteral administration.

EXAMPLE 4

In a round flask 0.1 mg N-acetylmuramyl-L-alanyl-D-isoglutaminyl-L-alanine-2-(1,2-dipalmitoyl-sn-glycero-3-hydroxyphosphoryloxy)-ethylamide (preparation according to European Patent Specification No. 25,495), 87.70 mg (0.098 mmol) disodium-N-[1,2-di-(9-cis-octadecenoyl)-sn-glycero-3-phosphoethanol]-N-hydroxysuccinylamine and 168.10 mg (0.226 mMol) 1,2-di-(9-cis-octadecenoyl)-sn-glycero-3-phosphoethanolamine are dissolved in a sufficient amount of sterile tert-butanol until all components are dissolved. The solution is filtered under sterile conditions over Acrodisc ® filter ($2.0 \times 10^{-7}$ m) and is bottled in a sterile vial. The vial is rotated at 1750 rmp and the solvent is blown off in a stream of purified, filtered (at the pressure of 1 bar) dry nitrogen. The vial is evacuated in a high vacuum of $6.0 \times 10^{-2}$ mbar and is sealed under argon inert gas atmosphere.

To this vial containing a thin film of the components mentioned above 10 ml of a sterile, phosphate buffered (pH 7.2–7.4), calcium free sodium chloride solution (Dulbecco) are added with a sterile syringe. This vial is then shaken for 10 minutes on a standardized laboratory shaker (Vortex, speed 6). The liposome dispersion obtained is storage stable at 4° and is suitable for parenteral administration.

EXAMPLE 5

In a round flask 0.1 mg N-acetylmuramyl-L-alanyl-D-isoglutaminyl-L-alanine-2-(1,2-dipalmitoyl-sn-glycero-3-hydroxyphosphoryloxy)-ethylamide (preparation according to European Patent Specification No. 25,495), 84.70 mg (0.098 mmol) disodium-N-[1,2-di-(9-cis-octadecenoyl)-sn-glycero-3-phosphoethanol]-N-hydroxysuccinylamine and 168.10 mg (0.226 mmol) 1,2-di-(9-cis-octadecenoyl)-sn-glycero-3-phosphoethanolamine are dissolved in a sufficient amount of sterile tert-butanol until all components are dissolved. The solution is filtered under sterile conditions over Acrodisc ® filter (2.0×10⁻⁷ m) and is bottled in a sterile vial. This vial is frozen at −45°. A vacuum is applied to the frozen vial and the solvent is removed until room temperature has been reached. The vial is sealed under argon inert gas atmosphere.

To this vial containing a lyophilisate of the components mentioned above 10 ml of a sterile, phosphate buffered (pH 7.2–7.4), calcium free sodium chloride solution (Dulbecco) are added with a sterile syringe. The vial is then shaken for 10 minutes on a standardized laboratory shaker (Vortex, speed 6). The liposome dispersion obtained is storage stable at 4° and is suitable for parenteral administration.

EXAMPLE 6

In a manner analogous to Examples 4 or 5 liposome dispersions are prepared containing 0.1 mg to 10 mg N-acetylmuramyl-L-alanyl-D-isoglutaminyl-L-alanine-2-(1,2-dipalmitoyl-sn-glycero-3-hydroxyphosphoryloxy)-ethylamide, 84.70 mg (0.098 mmol) disodium-N-[1,2-di-(9-cis-octadecenoyl)-sn-glycero-3-phosphoethanol]-N-hydroxysuccinylamine and 168.10 mg (0.226 mmol) 1,2-di-(9-cis-octadecenoyl)-sn-glycero-3-phosphoethanolamine.

EXAMPLE 7

In a manner analogous to Example 1 liposome dispersions are prepared containing 86.3 mg (0,098 mmol) disodium-N-[1,2-di-(9-cis-octadecenoyl)-sn-glycero-3-phosphoethanol]-N-hydroxyglutarylamine and 168.1 mg (0,026 mmol) 1,2-di-(9-cis-octadecenoyl)-sn-glycero-3-phosphoethanolamine and 0.1 mg up to 10 mg N-acetyl-muramyl-L-alanyl-D-isoglutamine-sodium salt or 0.1 mg up to 10 mg N-acetyl-desmethylmuramyl-L-alanyl-D-isoglutamine sodium salt.

What is claimed is:

1. A pharmaceutical liposome composition comprising
   (a) a first phospholipid of the formula:

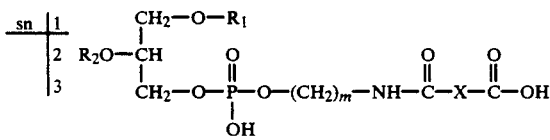

wherein m is 2 or 3;
   each of $R_1$ and $R_2$, independently of the other, is alkyl, alkenyl, or acyl of from 10 to 20 carbon atoms;
   X is a direct bond, $C_1$–$C_4$ alkylene which is unsubstituted or substituted with hydroxy, or $C_2$–$C_4$ alkenylene which is unsubstituted or substituted with hydroxy;
   or a pharmaceutically acceptable salt of said first phospholipid;
   (b) a second phospholipid of the formula:

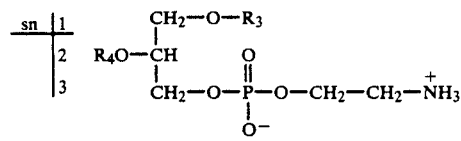

wherein each of $R_3$ and $R_4$, independently of the other, is the acyl group of a carboxylic acid of from 10 to 20 carbon atoms which is saturated, mono-unsaturated, or di-unsaturated, said second phospholipid being present with respect to said first phospholipid in a mole percent ratio of from about 90:10 to about 50:50;
   (c) one or more immunomodulators, the ratio of the molar amount of said immunomodulators to the total molar amount of said first and second phospholipids being from about 0.0001:1 to about 0.1:1; and
   (d) a pharmaceutically acceptable carrier solution, the pH of which is buffered to from 7.0 to 7.8.

2. A pharmaceutical liposome composition according to claim 1 wherein
   in said first phospholipid, m is 2 and X is unsubstituted $C_1$–$C_4$ alkylene, hydroxy substituted $C_1$–$C_4$ alkylene, or unsubstituted $C_2$–$C_4$ alkenylene;
   in said second phospholipid, each of $R_3$ and $R_4$, independently of the other, is straight chained alkanoyl or alkenoyl of from 10 to 20 carbon atoms, said second phospholipid being present with respect to said first phospholipid in a mole percent ratio of about 70:30; and
   the ratio of the molar amount of said immunomodulators to the total molar amount of said first and second phospholipids is from about 0.05:1 to about 0.1:1.

3. A pharmaceutical liposome composition according to claim 2 wherein in said first phospholipid, X is unsubstituted $C_1$–$C_4$ alkylene or unsubstituted $C_2$–$C_4$ alkenylene.

4. A pharmaceutical liposome composition according to claim 3 wherein in said first phospholipid, each of $R_1$ and $R_2$, independently of the other, is alkanoyl or alkenoyl having 10, 12, 14, 16, 18, or 20 carbon atoms; and in said second phospholipid, each of $R_3$ and $R_4$, independently of the other, is alkanoyl or alkenoyl having 10, 12, 14, 16, 18, or 20 carbon atoms.

5. A pharmaceutical liposome composition according to claim 4 wherein in said first phospholipid, each of $R_1$ and $R_2$, independently of the other, is 9-cis-dodecenoyl, 9-cis-tetradecenoyl, 6-cis-octadecenoyl, 6-trans-octadecenoyl, 9-cis-octadecenoyl, 9-trans-octadecenoyl, 11-cis-octadecenoyl, or 9-trans-icosenoyl, and X is 1,2-ethylene, 1,3-propylene, or vinylene, and in said second phospholipid, each of $R_3$ and $R_4$, independently of the other, is 9-cis-dodecenoyl, 9-cis-tetradecenoyl, 6-cis-octadecenoyl, 6-trans-octadecenoyl, 9-cis-octadecenoyl, 9-trans-octadecenoyl, 11-cis-octadecenoyl, or 9-trans-icosenoyl.

6. A pharmaceutical liposome composition according to claim 5 wherein said first phospholipid is either sodium N-[1,2-di-(9-cis-octadecenoyl)-sn-glycero-3-phosphoethanol]-N-hydroxysuccinylamine or sodium N-[1,2-di-(9-cis-octadecenoyl)-sn-glycero-3-phosphoethanol]-N-hydroxyglutarylamine and said second phospholipid is 1,2-di-(9-cis-octadecenoyl)-sn-glycero-3-phosphoethanolamine.

7. A pharmaceutical liposome composition according to claim 6 wherein said immunomodulators are selected from the group consisting of human gamma interferon and interleukine 2.

8. A pharmaceutical liposome composition according to claim 6 wherein said immunomodulators are selected from the group consisting of N-acetylmuramyl-L-alanyl-D-isoglutaminyl-L-alanine-2-(1,2-dipalmitoyl-sn-glycero-3-hydroxyphosphoryloxy)-ethylamide, N-acetylmuramyl-L-alanyl-D-glutamic acid-(Cγ-L-alanine-2-(1,2-dipalmitoyl-sn-glycero-3-hydroxyphosphoryloxy)-ethylamide)disodium salt, N-acetylmuramyl-L-alanyl-D-isoglutamine sodium salt, N-acetyldesmethylmuramyl-L-alanyl-D-isoglutamine sodium salt, N-acetylmuramyl-L-alanyl-D-isoglutamine-α-n-butyl ester, Nα-(N-acetylmuramyl-L-alanyl-D-isoglutaminyl)-Nγ-stearoyl-L-lysine, 6-O-stearoyl-N-acetylmuramyl-L-alanyl-D-isoglutamine, and lymphokines.

9. A pharmaceutical liposome composition according to claim 8 wherein said immunomodulators are selected from the group consisting of N-acetylmuramyl-L-alanyl-D-isoglutaminyl-L-alanine-2-(1,2-dipalmitoyl-sn-glycero-3-hydroxyphosphoryloxy)-ethylamide, N-acetylmuramyl-L-alanyl-D-isoglutamine sodium salt, and N-acetyldesmethylmuramyl-L-alanyl-D-isoglutamine sodium salt.

10. A composition according to claim 9 wherein the immunomodulator is N-acetyldesmethylmuramyl-L-alanyl-D-isoglutamine sodium salt.

11. A homogeneous mixture for preparation of a pharmaceutical liposome composition which comprises
(a) a first phospholipid of the formula:

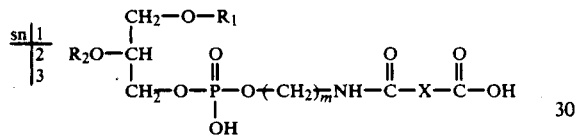

wherein m is 2 or 3;
each of $R_1$ and $R_2$, independently of the other, is alkyl, alkenyl, or acyl of from 10 to 20 carbon atoms;
X is a direct bond, $C_1$-$C_4$ alkylene which is unsubstituted or substituted with hydroxy, or $C_2$-$C_4$ alkenylene which is unsubstituted or substituted with hydroxy;
or a pharmaceutically acceptable salt of said first phospholipid;
(b) a second phospholipid of the formula:

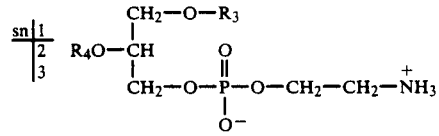

wherein each of $R_3$ and $R_4$, independently of the other, is the acyl group of a carboxylic acid of from 10 to 20 carbon atoms which saturated, mono-unsaturated, or di-unsaturated, said second phospholipid being present with respect to said first phospholipid in a mole percent ratio of about 70:30; and
(c) one or more immunomodulators, the ratio of the molar amount of said immunomodulators to the total molar amount of said first and second phospholipids of being from about 0.0001:1 to about 0.1:1.

* * * * *